United States Patent [19]

Yokoo et al.

[11] Patent Number: 4,985,544
[45] Date of Patent: Jan. 15, 1991

[54] PROCESS FOR RENATURING FISH GROWTH HORMONE

[75] Inventors: Yoshiharu Yokoo, Kanagawa; Seiji Sugimoto, Tokyo, both of Japan

[73] Assignee: Kyowa Hakko Kogyo Co., Ltd., Tokyo, Japan

[21] Appl. No.: 227,326

[22] Filed: Aug. 2, 1988

[30] Foreign Application Priority Data

Aug. 4, 1987 [JP] Japan ................... 62-194607

[51] Int. Cl.$^5$ .................. C07K 15/08; C07K 3/18; C07K 3/26; C07K 3/28
[52] U.S. Cl. ................... 530/399; 530/408; 530/409; 530/410; 530/412; 530/414; 530/415; 530/416; 530/417; 530/350; 435/69.4
[58] Field of Search ........... 435/68, 69.4; 530/408, 530/409, 410, 412, 414, 415, 416, 417, 350, 399

[56] References Cited

U.S. PATENT DOCUMENTS

| 4,530,787 | 7/1985 | Shaked et al. ............... 260/112 R |
| 4,652,630 | 3/1987 | Bentle et al. ............... 530/344 |
| 4,766,205 | 8/1988 | Ghosh-Dastidar ........... 530/402 |

FOREIGN PATENT DOCUMENTS

| 0114506 | 8/1984 | European Pat. Off. . |
| 0192629 | 2/1986 | European Pat. Off. . |
| 0166444 | 6/1986 | European Pat. Off. . |
| 0209068 | 9/1987 | European Pat. Off. . |

OTHER PUBLICATIONS

J. Bacteriology, 108, 553–563 (1971), p. 11, line. 5.
JP-A-61-93197, p. 17, line. 6.
Proc. Natl. Acad. Sci. U.S.A., 82, 4306 (1985), p. 18, line. 6.
Archives of Biochem. and Biophys., 244, 542 (1986), p. 18, line 3.
General and Comparative Encodrinol., 65, 478 (1987), p. 23, line 12.
Bio/Technology, 2, 800 (1984), p. 1, line 7.
Biochemistry, 24, 7662 (1985), p. 1, line 6.
Bio/Technology, 3, 643 (1985), p. 2, line 11.
DNA, 4, 273 (1985), p. 2, line 12.
JP-A-61-257931, p. 2, line 12.
"Tanpakushitsu Bunshi", 99–127, Iwanami Shoten (1985), p. 2, line 15.
Eur. J. Biochem., 163, 313–321 (1987), p. 4, line 7.
Biochimica et Biophysica Acta, 214, 498–508 (1970), p. 5, line 5.
JP-A-60-244259, p. 6, last line.
Busshitsu no Tanri to Seisei (Isolation and Purification of Substances), edited by Todai Shuppan, 145–155 (1977), p. 9, lines 14–16.
Methods in Enzymology, vol. 107, 1984, pp. 305–329; Academic Press, Inc., N.Y., T. E. Creighton "Disulfide Bond Formation in Proteins", pp. 307–312.
Biochemistry, vol. 25, 1986, pp. 6907–6917, American Chemical Society; T. F. Holzman et al., "Reoxidation of Reduced Bovine Growth Hormone from a Stable Secondary Structure", p. 6908, Experimental Procedures.

Primary Examiner—Margaret Moskowitz
Assistant Examiner—Keith C. Furman
Attorney, Agent, or Firm—Nixon & Vanderhye

[57] ABSTRACT

Reactivation of cysteine-containing protein in a process, in which a reduced and denatured cysteine-containing protein such as salmon growth hormone I or eel growth hormone I can be efficiently reactivated.

11 Claims, No Drawings

4,985,544

PROCESS FOR RENATURING FISH GROWTH HORMONE

FIELD OF THE INVENTION

This invention relates to a process for reactivating a reduced and denatured cysteine-containing protein.

BACKGROUND OF THE INVENTION

A protein is a biopolymer which exerts a specific function through the formation of a definite high-order structure which will be called a "natural form" hereinafter. A disulfide bond between cysteine residues involved in the above-mentioned high-order structure plays an important role in the performance of the function of the protein or in stabilizing the same. Recent development in gene recombination techniques has increased the production of proteins. In an expression system using *Escherichia coli*, in particular, a protein in the form of inclusion bodies is produced within the cells of the microorganism [cf. F.A.O. Marston et al., *BIO/TECHNOLOGY*, 2, 800 (1984); and D. N. Brems et al., *Biochemistry*, 24, 7662 (1985)]. Thus, it is an important problem to collect the desired protein from these inclusion bodies. In order to solubilize these proteinaceous inclusion bodies, it is necessary to once denature the same. When a cysteine-containing protein is to be solubilized, it is necessary to denature this protein in a reduced state. Thus, disulfide bonds should be formed at the same sites as those observed in the corresponding natural protein in order to efficiently reactivate the reduced and denatured protein.

A conventional process for converting a denatured protein into a natural one in the presence of a denaturing agent is carried out by diluting or dialyzing the starting protein with a solution free from any denaturing agent via one or more steps to thereby reactivate the same [cf. J. A. Gill et al., *BIO/TECHNOLOGY*, 3, 643 (1985); H. J. George et al., DNA, 4, 273 (1985); and JP-A-61-257931 (the term "JP-A" as used herein means an "unexamined published Japanese patent application")], since this transformation would frequently proceed in two-states [cf. Tanpakushitsu Bunshi (Protein Molecules), 99–127, Iwanami Shoten (1985)]. In this process, secondary and tertiary structures of the protein are also formed at the same time. Thus, hydrophobic groups, which are enclosed in protein molecules in the natural protein, would interact with each other or intermolecular or intramolecular disulfide bonds would be formed at sites different from those observed in the natural one. As a result, not the desired natural protein but an associated or denatured one would be frequently obtained. In the case of a protein having a marked tendency to form an associated or denatured material through the interaction between hydrophobic groups, in particular, the formation of disulfide bonds at the same sites as those of the natural one is considerably suppressed and thus the desired natural protein is obtained sometimes at a yield as low as approximately 1%.

Therefore, it is difficult to efficiently reactivate a reduced and denatured cysteine-containing protein, which is liable to be converted into an associated or denatured one, by the interaction between hydrophobic groups by a conventional reactivating process.

K. E. Langley et al. reported that a protein can be reactivated by forming disulfide bonds in a denatured protein at the same sites as those of the corresponding natural protein and at a high frequency, compared with the case in which the formation of disulfide bonds at the same sites as those of the natural one is inhibited by the formation of an associated or denatured one through the interaction between hydrophobic groups.

The process for reactivating bovine growth hormone of K. E. Langley et al. comprises (1) washing proteinaceous inclusion bodies produced within the cells of *Escherichia coli*, followed by solubilizing the inclusion bodies in 6 M guanidine hydrochloride; (2) oxidizing the inclusion bodies by allowing to stand at room temperature for 20 hours or more so that the formation of disulfide bonds occurs; (3) subjecting to gel filtration in the presence of 6 M guanidine hydrochloride; (4) collecting the monomer-containing fractions; and (5) diluting the fractions to the extent that the guanidine hydrochloride concentration is 2 M, followed by dialysis [K. E. Langley et al., Eur. J. Biochem , 163, 313–321 (1987)]. However, this process has such a disadvantage that since no reducing agent is added at the solubilization of the inclusion bodies, yields of the reduced monomer are low and formation of disulfide bonds at the same sites as those of the natural one is inhibited due to the action of the associated materials of the desired protein and substances contaminating the inclusion bodies which undesirably block the SH groups of the desired protein. Also, during oxidation of the inclusion bodies by allowing to stand at room temperature for 20 hours or more, aspargine residues and glutamine residues are deamidated [Biochemica. et Biophysica. Acta., 214, 498–508 (1970)]. If the oxidation is carried out at a low temperature, i.e., about 5° C., in order to prevent the aspargine and glutamine residues from deamidation, it would take a prolonged time for oxidation.

SUMMARY OF THE INVENTION

An object of the present invention is to provide a process for reactivating a reduced and denatured cysteine-containing protein in the desired natural form at a high yield.

We have found that reduced monomer of cysteine-containing protein can increase and the associated materials of the protein can decrease or disappear by adding a reducing agent as well as a denaturing agent at the solubilization of the protein. Also, we have found that substances contaminating the inclusion bodies of the desired protein produced within the cells of microorganisms, which undesirably block the SH groups of the desired protein, can be dissociated from the desired protein, by adding a reducing agent as well as a denaturing agent at the solubilization of the inclusion bodies, and the substances can be removed together with the reducing agent As the result, the denatured cysteine-containing protein can be reactivated in the desired natural form at high yield when disulfide bonds are formed in the denatured protein at the same sites as those of the corresponding natural protein. Thus, the present invention was completed.

The process of the present invention comprises the operative steps of: (1) converting a cysteine-containing protein into a reduced and denatured one by adding a denaturing agent and a reducing agent thereto to solubilize the same; (2) removing the reducing agent; (3) oxidizing the protein as denatured to form disulfide bonds at the same sites as those observed in the corresponding natural protein; and (4) removing the denaturing agent to isolate and purify the desired reactivated natural protein. The process of the present invention is particularly suitable for reactivating slightly soluble cysteine-containing proteins having few disulfide bonds and no intermolecular disulfide bond, which is liable to be converted into an associated or denatured one when reactivated in the presence of a denaturing agent at a low concentration, such as salmon growth hormone I (SGH-I) or eel growth hormone I.

DETAILED DESCRIPTION OF THE INVENTION

The protein in the form of inclusion bodies produced within the cells of microorganisms can be isolated and purified in accordance with the following method as described in JP-A-60-244259.

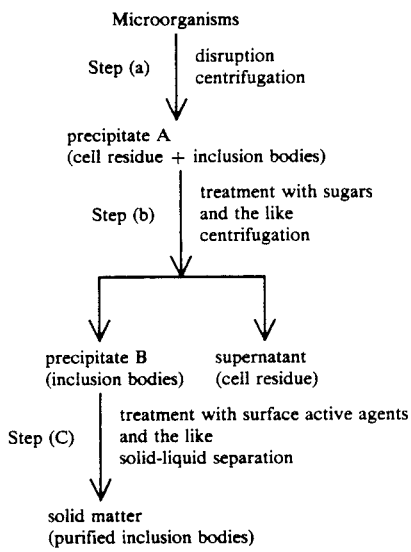

Each step of the isolation and purification of inlcusion bodies is described in detail below.

In step (a), the cells of microorganisms in which the proteinaceous inclusion bodies have been produced are disrupted and centrifuged to obtain precipitate (precipitate A).

The cells are suspended in a buffer solution having a neutral pH value (e.g., phosphate buffer having a pH value of 7) and subjected to various known disruption method such as sonication, lysozyme treatment, homogenization, disruption by mechanical compression. The cell disruption is preferably carried out using the compressor such as French press, Manton-Gaulin homogenizer under the appropriate conditions for each apparatus.

Then, the thus-obtained suspension is centrifuged to give precipitate A which contains proteinaceous inclusion bodies and cell residues. Centrifugation can be carried out using the conventional centrifuge generally at 2,000 to 15,000 rpm for 10 to 120 minutes, and preferably at 4,000 to 12,000 rpm for 30 to 90 minutes. Continuous type centrifuge such as a centrifuge using SCHARPLES ® can also be employed. A "SCHARPLES" type centrifuge is a high-speed tubular-bowl centrifuge with operating speeds of up to 18,000 rpm and centrifugal force of up to 20,000 G.

In step (b), the precipitate A thus obtained is suspended in an aqueous solution having dissolved therein solute selected from an alkali metal or alkaline earth metal salt of an inorganic acid, sugars such as pentose, hexose, di-saccharides, trisaccharides, deoxysugars, sugar alcohols, dextran, dextrin, or "FICOLL ®", and "PERCOLL" ®. Then, the suspension is centrifuged to obtain precipitate B containing protenaceous inclusion bodies. Supernatant containing cell residues is decanted. Conventionally, separation of cell components each of which has different density is conducted utilizing sucrose density-gradient centrifugation method, sucrose density-gradient equilibrium centrifugation method, or differential centrifugation method which comprises homogenizing rat liver in a sucrose-containing solution and centrifuging the homogenate to obtain precipitate containing cell nucleus [as described in Nozomi Otake et al., "Busshitsu no Tanri to Seisei (Isolation and Purification of Substances)", edited by Todai Shuppan, 145-155 (1977)].

In alkali metal or alkaline earth metal salts of an inorganic acid, examples of alkali metal or alkaline earth metal include sodium, potassium, calcium and cesium and examples of an inorganic acid include hydrochloric acid, sulfuric acid and hydrobromic acid. Specific examples of these salts include cesium chloride, calcium sulfate, sodium chloride and sodium bromide.

Examples of sugars include pentose such as L-arabinose, D-xylose and D-ribose; hexose such as D-glucose, D-mannose, D-galactose, L-galactose, D-fructose and L-sorbose; di- or trisaccharides such as sucrose, maltose, lactose, trehalose, cellobiose and raffinose; deoxysugars such as L-rhamnose and 2-deoxy-D ribose; and sugar alcohols such as glycerol, erythritol, arabitol, D-sorbitol and D-mannitol.

Ficoll and Percoll are trade names of the products manufactured by Pharmacia Fine Chemicals. Ficoll is a highly water-soluble synthetic macromolecule consisting of sucrose and epichlorohydrin. "PERCOLL" consists of colloidal silica particles of 15-30 nm diameter which have been coated with polyvinylpyrrolidone.

Solvents for the solution (suspension) containing the above-described solutes are preferably buffer solutions having a neutral pH value.

The solid concentration of the solution (suspension) ranges from 5 to 50 w/w% in the case of alkali metal or alkaline earth metal salts of inorganic acid; 10 to 80 w/w% in the case of glycerol; 5 to 50 w/w% in the case of dextran or dextrin; 0.25 to 4 M, preferably 0.5 to 2 M in the case of the other sugars. The solution or suspension is used in an amount of 1/20 to 20-folds (v/v) of the starting volume of cultures applied to step (a).

The thus-obtained suspension of precipitate A may be immediately subjected to centrifugation to obtain precipitate B. Preferably, the suspension is centrifuged after sufficient agitation for effective separation of precipitate B. The centrifugation can be carried out using the conventional centrifuge at 2,000 to 15,000 rpm for 10 to 120 minutes, preferably at 4,000 to 12,000 rpm for 30 to 90 minutes. Continuous type centrifuge such as a centrifuge using SCHARPLES ® can also be used.

In step (c), precipitate B is mixed with an aqueous solution containing a nonionic surface active agent, or cholic acids or an alkali metal salt of cholic acid, followed by solid-liquid separation to thereby remove the membrane components (including protein, lipid or lipopolysaccharide) of microorganisms contaminating precipitate B and purify the inclusion bodies.

Lipopolysaccharide is known as pyrogen and therefore, it is necessary to remove lipopolysaccharide from the inclusion bodies in view of use for pharmaceutical preparations. Schnaitman reported that proteins, lipids and lipopolysaccharides can be removed from the membrane of *Escherichia coli* by treating with Triton X-100, EDTA, etc. [J. Bacteriology, 108, 553 (1971)].

Examples of nonionic surface active agents include polyoxyethylene alkyl ethers such as polyoxyethylene oleyl ether [$C_{18}H_{35}O(CH_2CH_2O)_nH$, trade name: Brij 96 (n=10), Brij 98 (n=20), etc.], polyoxyethylene fatty acid esters such as polyoxyethylene stearate (trade name: NISSAN NONION S) polyoxyethylene alkyl phenyl ethers such as polyoxyethylene p-t-octylphenyl ether represented by the formula

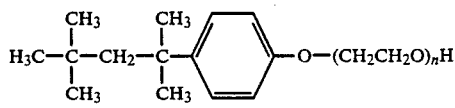

(trade name: TRITON X-100 (n=9, 10), sorbitan fatty acid esters such as sorbitan monostearate (trade name: SPAN 60), polyoxyethylene sorbitan fatty acid esters such as polyoxyethylene sorbitan monolaurate [trade name: "TWEEN 20" (having 20 units of oxyethylene)].

Examples of cholic acid or alkali metal salt thereof include cholic acid, deoxycholic acid and sodium salt thereof.

These surface active agents (including cholic acid and alkali metal salt thereof) are preferably dissolved in a buffer solution having a neutral pH value so as to give a final concentration of 0.2 to 10 w/v%, preferably 0.5 to 4 w/v%.

The thus-obtained mixture containing precipitate B can be immediately subjected to solid-liquid separation. Preferably, the separation is performed after the mixture is sufficiently agitated for efficient separation.

The solid-liquid separation can be effected by centrifugation or filtration. The conditions for the centrifugation is not restricted as long as liquid and solid can be separated. For example, centrifugation method as described in steps (a) and (b) can be employed.

At the treatment with the surface active agent, a metal chelating agent can be used in combination for efficient purification.

Examples of the metal chelating agent include EDTA (ethylenediaminetetraacetic acid), EGTA [ethyleneglucose bis(2-aminoethylene)tetraacetic acid], NTA (nitrilotriacetic acid), HEDTA (2-hydroxyethylethylenediaminepentaacetic acid), DCTA (1,2-diaminocyclohexanetetraacetic acid). The concentration of the metal chelating agent ranges from 2 to 50 mM, preferably 5 to 20 mM. The other conditions can be the same as those described in the case that the surface active agent is used alone.

The thus-recovered proteinaceous inclusion bodies are solubilized by adding a reducing and a denaturing agent.

One or more materials selected from among SDS (sodium dodecyl sulfate), urea, guanidine hydrochloride, acids and alkalis are employed as a denaturing agent. The denaturing agent and its concentration are selected in such a manner as to render the protein to be solubilized as uniform as possible. When acids or alkalis are used as a denaturing agent, solvents used are not particularly restricted. When the denaturing agent other than acids and alkalis are used, preferred examples of the solvents are buffer solutions having an approximately neutral pH value (e.g., a phosphate buffer having a pH value of 7). The reducing agent, which may be selected from, for example, monovalent thiols such as β-mercaptoethanol, cysteine and glutathione or dithiothreitol (DTT), is added to an aqueous solution containing the denaturing agent. Among these substances, DTT is particularly preferable since it has little tendency to form a disulfide bond with a cysteine residue of a protein.

By adding a reducing agent as well as a denaturing agent at the solubilization of a protein, reduced monomer of the protein can increase and the associated materials of the protein can decrease or disappear. Substances contaminating the inclusion bodies of the desired protein produced within the cells of microorganisms, which undesirably block the SH groups of the desired protein, can also be dissociated from the desired protein, by adding a reducing agent as well as a denaturing agent at the solubilization of the inclusion bodies.

The reducing agent may be removed by, for example, dilution, dialysis involving ultrafiltration, gel filtration, chromatography involving absorption/desorption or a batch process, each in the presence of a denaturing agent under non-oxidizing conditions, though it is not restricted thereby. Gel filtration is particularly preferable.

Also, the substances contaminating the inclusion bodies produced within the cells of microorganisms, which block the SH groups of the desired protein, can be removed together with the reducing agent.

The oxidation process is not particularly restricted. It may be carried out spontaneously. Alternately, it may be effected by bubbling oxygen or air into the aqueous solution to accelerate the oxidation by the dissolved oxygen; adding divalent copper ions to the aqueous solution to accelerate the oxidation by the dissolved oxygen; or by adding a weak oxidizing agent such as o-iodosobenzoic acid, oxidized glutathione, a mixture of oxidized glutathione and reduced glutathione, cystine or a mixture of cystine and cysteine to the aqueous solution. It is further possible to control the oxidation rate by adjusting the pH value. At the oxidation, it is preferable that the protein concentration is as low as possible. The protein concentration may be 0.1 to 2,000 μg/ml in general, though it may vary depending on the protein to be recovered. The reaction period and reaction temperature are not particularly restricted. It is generally preferable to effect the reaction at a temperature of below 10° C. without freezing the reaction solution for five minutes to ten hours. By this oxidation, a protein having disulfide bonds at the same sites as those observed in the corresponding natural protein at a high frequency is formed.

The denaturing agent may be removed by, for example, dilution, dialysis involving ultrafiltration, gel filtration, isoelectric precipitation, chromatography involving absorption/desorption or a batch process. Thus, associated or denatured proteins having disulfide bonds at sites different from those observed in the natural one, as well as impurities, are removed together with the denaturing agent, since these materials are different in, for example, molecular weight, charge or hydrophobic nature from the desired protein. Thus, the protein having disulfide bonds at the same sites as those observed in the corresponding natural protein can be readily and reliably isolated. More particularly, the isolation may be carried out by, for example, (a) dialysis/centrifugation, (b) dilution/concentration/isoelectric precipitation/centrifugation, (c) ion exchange chromatography/dialysis/centrifugation, or (d) gel filtration/ion exchange chromatography.

Through the process of the present invention, the reaction temperature is not particularly restricted. Preferably, the reaction can be carried out at a temperature of below 10° C. without freezing the reaction solution. The pH value of a solution containing the protein to be reactivated is not particularly restricted, but it varies depending on the kind of the protein. Preferably, the pH value of the solution ranges from 2 to 10.

To further illustrate the present invention, and not b way of limitation, the following examples will be given.

EXAMPLE 1

Reactivation of SGH-I from inclusion bodies produced by *E. coli*

Recombinamt SGH-I was isolated from recombinant SGH-I inclusion body-containing cells obtained by a culture method described in JP-A-61-93197 and purified to a purity of 90% according to a method described in JP-A-60-224259. 5 mg of these inclusion bodies were dissolved in a 100 mM tris [tris(hydroxymethyl-)aminomethane] buffer solution (pH 8.0) containing 7 M of urea, 5 mM of EDTA and 1 mM of DTT to give a volume of 2.5 ml. The resulting solution was stirred at 4° C. for two hours and then centrifuged at 12,000 rpm for five minutes The reducing agent was removed from the supernatant using a gel filtration column PD-10 (manufactured by Pharmacia Fine Chemicals PD-10 is a prepacked disposable column, which contains 9.1 ml of Sephadex G-25 Medium. Sephadex is a bead-formed gel prepared by cross-linking dextran with epichlorohydrin. The dry bead diameter of Sephadex G-25 Medium is 50–150 μm. The fractionation range (molecular weight) of Sephadex G-25 Medium is 1000–5000 for peptides and globular proteins) which had been equilibrated with a 100 mM tris buffer solution (pH 7.0) containing 7 M of urea. 3.5 ml of the protein-containing fraction thus obtained was mixed with the equivalent amount of a 100 mM tris buffer solution (pH 9.0) containing 7 M of urea and 1 mM of $CuSO_4$ and the obtained mixture was allowed to stand at 4° C. for two hours to thereby allow the oxidation to proceed. Then, 7 ml of this solution was dialyzed against 2 l of a 100 mM tris buffer solution (pH 7.0) at 4° C. overnight. After centrifuging the internal solution at 12,000 rpm for five minutes, almost pure recombinant SGH-I was collected in the supernatant. The activity of the recombinant SGH-I thus obtained was determined according to the process reported by Sekine et al. (cf. Proc. Natl. Acad. Sci. USA, 82, 4306 (1985)). As a result, the obtained recombinant SGH-I showed an activity comparable to that of natural SGH-I reported by H. Kawauchi et al. [cf. Archives of Biochem. and Biophys., 244, 542 (1986)]. Table 1 shows the yields.

TABLE 1

| Reactivation of salmon growth hormone I | | |
|---|---|---|
| Steps of Reactivation | Volume (ml) | Protein* (μg) |
| inclusion body solution | 2.5 | 1,130 |
| gel filtration fraction | 3.5 | 915 |
| oxidized solution | 7.0 | 900 |
| dialyzed and centrifuged supernatant | 7.5 | 503 |

*Note: amount of salmon growth hormone I

EXAMPLE 2

Purification of natural SGH-I after oxidation step (I)

The oxidized solution obtained in Example 1 was diluted 10-fold with a 100 mM tris buffer solution (pH 8.0) and allowed to stand at 4° C. for two hours. Then, it was concentrated to 1/10 by using an ultrafiltration membrane (YM-10: manufactured by Amicon YM-10 is an ultrafiltration membrane which consists of acetylcellulose membrane on a polyethylene support. The nominal molecular weight of YM-10 is 10000). The pH value of the concentrate was adjusted to 6.0 with 1 N hydrochloric acid to thereby induce isoelectric precipitation. After centrifuging at 12,000 rpm for five minutes, almost pure recombinant SGH-I was collected in the supernatant. The activity of the recombinant SGH-I thus obtained was determined according to the process reported by Sekine et al. [cf. Proc. Natl. Acad. Sci. USA., 82, 4306 (1985)]. As a result, the obtained recombinant SGH-I showed an activity comparable to that of natural SGH-I as reported by H. Kawauchi et al. [cf. Archives of Biochem and Biophys., 244, 542 (1986)]. Table 2 shows the yields.

TABLE 2

| Reactivation of salmon growth hormone I | | |
|---|---|---|
| Steps of Reactivation | Volume (ml) | Protein* (μg) |
| oxidized solution | 7.0 | 900 |
| isoelectric-precipitated and centrifuged supernatant | 7.8 | 473 |

*Note: amount of salmon growth hormone I

EXAMPLE 3

Purification of natural SGH-I after oxidation step (II)

The oxidized solution obtained in Example 1 was diluted 10-fold with 7 M urea and the pH value of the obtained solution was adjusted to 8.0. Then the solution was passed through a DEAE SEPHAROSE ® CL-6B column (1.5×5.7 cm, manufactured by Pharmacia Fine Chemicals DEAE-Sepharose CL-6B is based on Sepharose CL-6B, which is prepared from Sepharose 6B by reacting it with 2,4-dibromopropanol under strongly alkaline conditions and desulphating the resulting gel by alkaline hydrolysis under reducing conditions. The DEAE (diethylamino ethyl)-group is then attached to the gel by an ether linkage to the monosaccharide unit to give DEAE-Sepharose CL-6B. Sepharose 6B is a bead-formed gel prepared from agarose. The wet bead diameter of Sepharose 6B is 45–165 μm. The fractionation range of Sepharose 6B is 10,000–4,000,000 for proteins), which had been equilibrated with a 10 mM tris buffer (pH 8.0) containing 7 M urea, at a rate of 10 ml/hr. The column was then washed with 50 ml of the above buffer solution at a rate of 10 ml/hr and subsequently eluted by a concentration gradient method with the use of 30 ml of the above buffer solution and a 10 mM tris buffer solution (pH 8.0) containing 7 M of urea and 1 M of NaCl at at rate of 5 ml/hr. The elute was fractionated by 5 ml portions. As a result, almost pure recombinant SGH-I was collected in the third fraction (5 ml). 5 ml of this fraction was dialyzed against 1.5 l of a 100 mM tris buffer (pH 8.0) at 4° C. overnight. The internal solution was centrifuged at 12,000 rpm for five minutes. Recombinant SGH-I having the same stereostructure involving the position of disulfide bonds as natural SGH-I was collected in the supernatant. The activity of the recombinant SGH-I obtained was determined according to the process reported by Sekine et al. [cf. Proc. Natl. Acad. Sci. USA., 82, 4306 (1985)]. As a result, the obtained recombinant SGH-I showed an activity comparable to that of natural SGH-I as reported by H. Kawauchi et al. [cf. Archives of Biochem and Biophys., 244, 542 (1986)]. Table 3 shows the yields.

TABLE 3

Reactivation of salmon growth hormone I

| Steps of Reactivation | Volume (ml) | Protein* (μg) |
| --- | --- | --- |
| oxidized solution | 7.0 | 900 |
| DEAE-elution fraction | 5.0 | 433 |
| dialyzed and centrifuged supernatant | 7.8 | 389 |

*Note: amount of salmon growth hormone I.

EXAMPLE 4

Reactivation of eel growth hormone I from inclusion bodies produced by E. coli

Recombinant eel growth hormone I inclusion bodies were obtained by the following method. E. coli EUPA1 (FERM BP-825) was inoculated into 10 ml of an MCG medium (pH 7.2) comprising 0.6% of $Na_2HPO_4$, 0.3% of $KH_2PO_4$, 0 5% of NaCl, 0.1% of $NH_4Cl$, 0.5% of glucose, 0.5% of Casamino acid, 1 mM of $MgSO_4$ and 4 μg/ml of vitamin $B_1$ and cultured in the medium at 30° C. for seven hours. The culture thus obtained was inoculated into 50 ml of an MCG medium and further cultured in it at 30° C. for 18 hours. The culture obtained was inoculated into 1 l of an MCG medium and further cultured therein at 30° C. for five hours, then at 42° C. for two hours and finally at 37° C. for 41 hours. The culture thus obtained was centrifuged at 8,000 rpm for ten minutes to collect the cells. From these cells, eel growth hormone I inclusion bodies were isolated and purified at a purity of approximately 90% according to a method described in JP-A-60-244259.

5 mg of these inclusion bodies were dissolved in a 100 mM tris buffer solution (pH 8.0) containing 7 M of urea, 5 mM of EDTA and 1 mM of DTT to give a volume of 2.5 ml. The resulting solution was stirred at 4° C. for two hours and then centrifuged at 12,000 rpm for five minutes DTT was removed from the supernatant by using a gel filtration column PD-10 (manufactured by Pharmacia Fine Chemicals) which have been equilibrated with a 100 mM tris buffer solution (pH 7.0) containing 7 M of urea. 3.5 ml of the protein-containing fraction thus obtained was mixed with the equivalent amount of a 100 mM tris buffer solution (pH 9.0) containing 7 M of urea and 1 mM of $CuSO_4$ and the obtained mixture was allowed to stand at 4° C. for two hours to thereby allow the oxidation to proceed. Subsequently, 7 ml of this solution was dialyzed against 2 l of a 100 mM tris buffer solution (pH 7.0) at 4° C. overnight. After centrifuging the internal solution at 12,000 rpm for five minutes, almost pure recombinant eel growth hormone I was collected in the supernatant. The antibody-binding activity of the recombinant eel growth hormone I thus obtained was determined according to the radioimmunoassay reported by M. Kishida et al. [cf. General and Comparative Endocrinol., 65, 478 (1987)]. As a result, the obtained eel growth hormone I showed a biological activity comparable to that of natural eel growth hormone I reported by M. Kishida et al. [cf. General and Comparative Endocrinol., 65, 478 (1987)]. Table 4 shows the yields.

TABLE 4

Reactivation of eel growth hormone I

| Steps of Reactivation | Volume (ml) | Protein* (μg) |
| --- | --- | --- |
| inclusion body solution | 2.5 | 1,050 |
| gel filtration fraction | 3.5 | 930 |
| oxidized solution | 7.0 | 912 |
| dialyzed solution | 7.8 | 620 |

*Note: amount of eel growth hormone I.

EXAMPLE 5

Reactivation of SGH-I from inclusion bodies produced by E. coli

Recombinant SGH-I was isolated from recombinant SGH-I inclusion body-containing cells obtained by a culture method described in JP-A-61-93197 and purified to a purity of 90% according to a method described in JP-A-60-244259. 5 mg of these inclusion bodies were dissolved in a 100 mM tris buffer solution (pH 8.0) containing 7 M of urea, 5 mM of EDTA and 1 mM of DTT to give a volume of 2.5 ml. The resulting solution was stirred at 4° C. for two hours and then centrifuged at 12,000 rpm for five miutes. DTT was removed from the supernatant using a gel filtraiton column PD-10 (manufactured by Pharmacia Fine Chemicals) which had been equilibrated with a 100 mM tris buffer solution (pH 7.0) containing 7 M of urea. 3.5 ml of the protein-containing fraction thus obtained was mixed with the equivalent amount of a 100 mM tris buffer solution (pH 9.0) containing 7 M urea and 0.2 mM of oxidizing glutathione and the resulting mixture was stirred at 4° C. overnight to thereby allow the oxidation to proceed. Subsequently, 7 ml of this solution was dialyzed against 2 l of a 100 mM tris bufer solution (pH 7.0) at 4° C. overnight. After centrifuging the internal solution at 12,000 rpm for five minutes, almost pure recombinant SGH-I was collected in the supernatant. The activity of the recombinant SGH-I thus obtained was determined according to the process reported by Sekine et al. [cf. Proc. Natl. Acad. Sci USA., 82, 4306 (1985)]. As a result, the obtained recombinant SGH-I showed an activity comparable to that of natural SGH-I as reported by H. Kawauchi et al. [cf. Archives of Biochem. and Biophys., 244, 542 (1986)]. Table 5 shows the yields.

TABLE 5

Reactivation of salmon growth hormone I

| Steps of Reactivation | Volume (ml) | Protein* (μg) |
| --- | --- | --- |
| inclusion body solution | 2.5 | 1,130 |
| gel filtration fraction | 3.0 | 915 |
| oxidized solution | 7.0 | 900 |
| dialyzed and centrifuged supenatant | 7.5 | 510 |

*Note: amount of salmon growth hormone I.

REFERENCE EXAMPLE 1

Reactivation of salmon growth hormone I by conventional method 5 mg of SGH-I inclusion bodies obtained in the same manner as the one described in Example 1 were dissolved in a 100 mM tris buffer solution (pH 8.0) containing 7 M of urea, 5 mM of EDTA and 1 mM of DTT to give a volume of 12.5 ml. The obtained solution was stirred at 4° C. for two hours and centrifuged at 12,000 rpm for five minutes. The supernatant was dialyzed against 3 l of a 100 mM phosphate buffer solution (pH 7.0) at 4° C. overnight. The internal solution was centrifuged at 12,000 rpm for five minutes to give the supernatant. Table 6 shows the yields. Although the supernatant contains almost pure recombinant SGH-I, the yield was extremely low. Thus, this process was not effective in practice.

TABLE 6

Reactivation of salmon growth hormone I (conventional method)

| Steps of Reactivation | Volume (ml) | Protein* ($\mu$g) |
|---|---|---|
| inclusion body solution | 12.5 | 1,040 |
| dialyzed solution | 13.0 | 111 |

*Note: amount of salmon growth hormone I.

REFERENCE EXAMPLE 2

Reactivation of eel growth hormone I by conventional method 5 mg of recombinant eel growth hormone I inclusion bodies obtained in the same manner as the one described in Example 4 were dissolved in a 100 mM tris buffer solution (pH 8.0) containing 7 M of urea, 5 mM of EDTA and 1 mM of DTT to give a volume of 12.5 ml. The obtained solution was stirred at 4° C. for two hours and centrifuged at 12,000 rpm for five minutes. The supernatant was dialyzed against 3 l of a 100 mM phosphate buffer solution (pH 7.0) at 4° C. overnight. The internal solution was centrifuged at 12,000 rpm for five minutes to give the supernatant. Table 7 shows the yields. Although the supernatant contains almost pure recombinant eel growth hormone I, the yield was extremely low. Thus, this process was not effective in practice.

TABLE 7

Reactivation of eel growth hormone I (conventional method)

| Steps of Reactivation | Volume (ml) | Protein* ($\mu$g) |
|---|---|---|
| inclusion body solution | 12.5 | 1,070 |
| dialyzed solution | 13.0 | 325 |

*Note: amount of eel growth hormone I.

According to the present invention, a reduced and denatured cysteine-containing protein can be efficiently reactivated.

REFERENCE EXAMPLE 3

Reactivation of salmon growth hormone I by method of K. E. Langley et al [Eur. J. Biochem., 163, 313–321 (1987)]

100 mg of SGH-I inclusion bodies obtained in the same manner as the one described in Example 1 were dissolved in a 50 mM tris hydrochloride buffer solution (pH 8.0) containing 6 M of guanidine hydrochloride to give a volume of 10 ml. After allowing to stand for 80 hours, the SGH-I-containing solution was passed through a SEPHACRYL S-200 ® column (2.6×94 cm, manufactured by Pharmacia Fine Chemicals Sephacryl S-200 is prepared by covalently cross-linking allyl dextran with N,N'-methylene bisacrylamide. The wet bead diameter of Sephacryl S-200 Superfine is 40–105 $\mu$m. The fractionation range (molecular weight) is 5000–250000 for proteins), which had been equilibrated with the above-described tris hydrochloride buffer at a rate of 50 ml/hr and subsequently eluted with the same buffer. The elute was fractionated by 5 ml portions to obtain a total volume of the fraction of 35 ml. To this fraction, a buffer solution (pH 8.5) containing 0.25 w/v% of NaHCO$_3$, 0.2 w/v% of $\alpha$-lactose and 0.2 w/v% of mannitol were added to give a final volume of 105 ml. Then, the thus-obtained solution was dialyzed against 30 l of the above-described buffer at room temperature for 24 hours. The internal solution was centrifuged to obtain the supernatant. Table 8 shows the yields. Although almost pure recombinant SGH I was recovered in the supernatant, the yield was extremely low. Thus, this process was not effective in practice.

TABLE 8

Reactivation of salmon growth hormone I

| Steps of Reactivation | Volume (ml) | Protein* ($\mu$g) |
|---|---|---|
| inclusion body solution | 10 | 22,600 |
| oxidized solution | 10 | 22,600 |
| gel filtration fraction | 35 | 9,100 |
| dialyzed and centrifuged supenatant | 110 | 5,500 |

*Note: amount of salmon growth hormone I.

While the invention has been described in detail and with reference to specific embodiments thereof, it will be apparent to one skilled in the art that various changes and modifications can be made therein without departing from the spirit and scope thereof.

What is claimed is:

1. A process for renaturing a fish growth hormone polypeptide in its natural form which consists of the successive steps of:
    (1) converting a fish growth hormone polypeptide into the corresponding reduced and denatured protein by adding a denaturing agent and a reducing agent thereto to solubilize the protein;
    (2) removing the reducing agent;
    (3) oxidizing the protein, as denatured, to form disulfide bonds at the same sites as those observed in the corresponding natural protein; and thereafter
    (4) removing the denaturing agent to thereby isolate and purify the renatured protein.

2. A process of renaturing a fish growth hormone polypeptide in its natural form from inclusion bodies produced within the cells of a microorganism, said process consisting of the successive steps of: fractionation range (molecular weight) is 5000–250000 for proteins.

3. A process as set forth in claim 1 or 2, wherein said denaturing agent is selected from the group consisting of SDS, urea, guanidine hydrochloride, acids and alkalis.

4. A process as set forth in claim 1 or 2, wherein the reducing agent is removed in the presence of a denaturing agent under non-oxidizing conditions by dilution, dialysis, ultrafiltration, gel filtration, adsorption/desorption chromatography or a batch process of adsorption/desorption.

5. A process as set forth in claim 1 or 2, wherein the reducing agent is removed by gel filtration in the presence of a denaturing agent under non-oxidizing conditions.

6. A process as set forth in claim 1 or 2, wherein the oxidation process is spontaneous.

7. A process as set forth in claim 1 or 2, wherein said oxidation is carried out by a method selected from the group consisting of air-oxidation with aeration, air-oxidation with the use of a metal ion as a catalyst, and oxidation with the use of a weak oxidizing agent.

8. A process as set forth in claim 7, wherein said weak oxidizing agent is selected from the group consisting of o-iodosobenzoic acid, oxidized glutathione, a mixture of oxidized glutathione and reducing glutathione, cystine or a mixture of cystine and cysteine.

9. A process as set forth in claim 1 or 2, wherein the protein concentration during the oxidation step is from about 0.1 to about 2,000 μg/ml.

10. A process as set forth in claim 1 or 2, in which the cysteine-containing protein is salmon growth hormone I.

11. A process as set forth in claim 1 or 2, in which the cysteine-containing protein is eel growth hormone I.

* * * * *